US00PP18417P2

(12) United States Plant Patent
Klemm

(10) Patent No.: US PP18,417 P2
(45) Date of Patent: Jan. 15, 2008

(54) **NEW GUINEA *IMPATIENS* PLANT NAMED 'KLENI05081'**

(50) Latin Name: *Impatiens hawkeri*
Varietal Denomination: KLENI05081

(75) Inventor: Nils Klemm, Stuttgart (DE)

(73) Assignee: Kleninn + Sohn GmbH + Co. KG, Stuttgart, DE (US)

( * ) Notice: Subject to any disclaimer, the term of this patent is extended or adjusted under 35 U.S.C. 154(b) by 0 days.

(21) Appl. No.: 11/524,392

(22) Filed: Sep. 20, 2006

(51) Int. Cl.
*A01H 5/00* (2006.01)

(52) U.S. Cl. ..... Plt./318
(58) Field of Classification Search ..... Plt./318
See application file for complete search history.

*Primary Examiner*—Kent Bell
(74) *Attorney, Agent, or Firm*—C. A. Whealy

(57) ABSTRACT

A new and distinct cultivar of *Impatiens* plant named 'KLENI05081', characterized by its upright and outwardly spreading to trailing growth habit; rounded plant habit; freely branching habit; dark green-colored leaves; freely flowering habit; relatively large light pink and orange bi-colored flowers; and good garden performance.

1 Drawing Sheet

Botanical designation: *Impatiens hawkeri*
Cultivar denomination: 'KLENI05081'.

BACKGROUND OF THE INVENTION

The present invention relates to a new and distinct cultivar of New Guinea *Impatiens,* botanically known as *Impatiens hawkeri* and hereinafter referred to by the name 'KLENI05081'.

The new Impatiens is a product of a planned breeding program conducted by the Inventor in Stuttgart, Germany. The objective of the breeding program is to create new freely-branching New Guinea *Impatiens* cultivars with medium plant habit, early and freely flowering habit, and large and attractive flowers.

The new *Impatiens* originated from a cross-pollination made by the Inventor during the summer of 2002 in Stuttgart, Germany of a proprietary selection of *Impatiens hawkeri* identified as code number A 200, not patented, as the female, or seed, parent with a proprietary selection of *Impatiens hawkeri* identified as code number U 111, not patented, as the male, or pollen, parent. The new *Impatiens* was discovered and selected by the Inventor as a single flowering plant within the progeny of the stated cross-pollination in a controlled environment in Stuttgart, Germany in May, 2003.

Asexual reproduction of the new *Impatiens* by terminal cuttings in a controlled environment in Stuttgart, Germany since July, 2003, has shown that the unique features of this new *Impatiens* are stable and reproduced true to type in successive generations.

SUMMARY OF THE INVENTION

The cultivar KLENI05081 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'KLENI05081'. These characteristics in combination distinguish 'KLENI05081' as a new and distinct cultivar of *Impatiens:*

1. Upright and outwardly spreading to trailing growth habit; rounded plant habit.
2. Freely branching habit.
3. Dark green-colored leaves.
4. Freely flowering habit.
5. Relatively large light pink and orange bi-colored flowers.
6. Good garden performance.

Plants of the new *Impatiens* can be compared to plants of the female parent selection. Plant of the new *Impatiens* differ primarily from plants of the female parent selection in branching habit as plants of the new *Impatiens* were more freely branching.

Plants of the new *Impatiens* can be compared to plants of the male parent selection. Plants of the new *Impatiens* differ from plants of the male parent selection in the following characteristics:

1. Plants of the new *Impatiens* have larger flowers than plants of the male parent selection.
2. Plants of the new *Impatiens* and the male parent selection differ in flower color as plants of the male parent selection have light pink and violet bi-colored flowers.

Plants of the new *Impatiens* can be compared to plants of the *Impatiens* cultivar Palermo, not patented. In side-by-side comparisons conducted in Stuttgart, Germany, plants of the new *Impatiens* differed from plants of the cultivar Palermo in the following characteristics:

1. Plants of the new *Impatiens* had larger flowers than plants of the cultivar Palermo.
2. Plants of the new *Impatiens* and the cultivar Palermo differed in flower color as plants of the cultivar Palermo had light pink and red bi-colored flowers.

BRIEF DESCRIPTION OF THE PHOTOGRAPH

The accompanying colored photograph illustrates the overall appearance of the new *Impatiens,* showing the colors as true as it is reasonably possible to obtain in colored reproductions of this type. Colors in the photograph may differ slightly from the color values cited in the detailed botanical description which accurately describe the colors of the new *Impatiens*. The photograph comprises a side perspective view of typical flowering plants of 'KLENI05081' grown in a container.

DETAILED BOTANICAL DESCRIPTION

The photograph and following observations, measurements and values describe plants grown in Stuttgart, Germany, in containers and under commercial practice during the summer in a polypropylene-covered shadehouse with day temperatures ranging from 15° C. to 40° C. and night temperatures ranging from 8° C. to 20° C. Rooted young plants had been growing for about five months when the photograph and description were taken. In the following description, color references are made to The Royal Horticultural Society Colour Chart, 1995 Edition, except where general terms of ordinary dictionary significance are used.

Botanical classification: *Impatiens hawkeri* cultivar KLENI05081.

Parentage:

*Female, or seed, parent.*—Proprietary selection of *Impatiens hawkeri* identified as code number A 200, not patented.

*Male, or pollen, parent.*—Proprietary selection of *Impatiens hawkeri* identified as code number U 111, not patented.

Propagation:

*Type.*—By terminal cuttings.

*Time to initiate roots, summer.*—About ten days at temperatures of 20° C.

*Time to initiate roots, winter.*—About twelve days at temperatures of 20° C.

*Time to produce a rooted young plant, summer.*—About 18 days at temperatures of 20° C.

*Time to produce a rooted young plant, winter.*—About 21 days at temperatures of 20° C.

*Root description.*—Fine to medium, fibrous; creamy white in color.

*Rooting habit.*—Freely branching; dense.

Plant description:

*Plant and growth habit.*—Upright to outwardly spreading growth habit; rounded plant habit. Freely branching habit with about 16 to 18 lateral branches; pinching is typically not required. Vigorous growth habit.

*Plant height.*—About 23 cm.

*Plant diameter.*—About 54 cm.

Lateral branch description:

*Length.*—About 17 cm.

*Diameter.*—About 4 mm.

*Internode length.*—About 4.3 cm.

*Strength.*—Strong.

*Aspect.*—Initially upright to outwardly spreading.

*Texture.*—Smooth, glabrous.

*Color.*—187A.

Foliage description:

*Arrangement.*—Opposite or in whorls; simple.

*Length.*—About 12.5 cm.

*Width.*—About 2.6 cm.

*Shape.*—Oblong to lanceolate.

*Apex.*—Acuminate.

*Base.*—Attenuate.

*Margin.*—Serrate with ciliation.

*Texture, upper and lower surfaces.*—Smooth, glabrous; leathery.

*Venation pattern.*—Pinnate; arcuate.

*Color.*—Developing foliage, upper surface: 147A. Developing foliage, lower surface: 183C. Fully expanded foliage, upper surface: 139A; venation, 183B. Fully expanded foliage, lower surface: 138B; venation, 183B.

*Petiole length.*—About 2.4 cm.

*Petiole diameter.*—About 2.3 mm.

*Petiole texture, upper and lower surfaces.*—Smooth, glabrous.

*Petiole color, upper and lower surfaces.*—183B.

Flower description:

*Flower type and flowering habit.*—Single rounded axillary flowers. Freely flowering habit; usually about nine open flowers and flower buds per lateral branch. Flowers positioned above the foliage and typically face upright or outward. Flowers last about 10 to 14 days under greenhouse conditions. Petals self-cleaning, gynoecium persistent. Flowers not fragrant.

*Natural flowering season.*—Year-round under greenhouse conditions. In the garden, flowering from spring until fall in Germany. Plants begins flowering about 14 weeks after planting.

*Flower size.*—Length: About 5.8 cm. Width: About 5.9 cm. Depth: About 1.4 cm.

*Flower buds.*—Length: About 1.4 cm. Diameter: About 9 mm. Shape: Ovoid; pointed. Color: 42B.

*Petals.*—Quantity/arrangement: Five per flower in a single whorl. Length, banner petal: About 2.6 cm. Length, lateral petals: About 2.5 cm. Length, lower petals: About 3.1 cm. Width, banner petal: About 3.7 cm. Width, lateral petals: About 2.7 cm. Width, lower petals: About 2.5 cm. Shape: Cordate. Apex: Emarginate. Base: Acute. Margin: Entire. Texture, upper and lower surfaces: Smooth, glabrous. Color: When opening and fully opened, upper surface: Ground color, 55C; star pattern, 34A. With development, ground color, 55D; star pattern, 50A. When opening and fully opened, lower surface: 55C.

*Sepals.*—Quantity/arrangement: Three; one modified into an elongated spur. Length: About 1.3 cm. Width: About 6 mm. Shape: Oval. Apex: Acute. Base: Obtuse. Margin: Entire. Texture, upper and lower surfaces: Smooth, glabrous. Color, upper surface: 147C. Color, lower surface: 182B. Spur length: About 3.5 cm. Spur diameter: At flower, about 2 mm; at apex, less than 1 mm. Spur texture: Smooth, glabrous. Spur color: 180D.

*Peduncles.*—Length: About 4.3 cm. Diameter: About 1.5 mm. Angle: About 45° from vertical. Strength: Strong. Texture: Smooth, glabrous. Color: 177D.

*Reproductive organs.*—Stamens: Quantity: Five fused at anthers; filaments free. Anther size: About 6 mm by 3.5 mm. Anther color: 57C. Pollen amount: Abundant. Pollen color: 158B. Pistils: Quantity per flower: One. Pistil length: About 5 mm. Stigma shape: Rounded. Stigma color: 158A. Style color: 158A. Ovary color: 147A.

*Seed/fruit.*—Seed and fruit production have not been observed.

Disease/pest resistance: Plants of the new *Impatiens* have not been observed to be resistant to pathogens and pests common to New Guinea *Impatiens*.

Garden performance: Plants of the new *Impatiens* have been observed to have good garden performance and tolerate wind, rain and temperatures ranging from about 4° C. to about 40° C.

It is claimed:

1. A new and distinct *Impatiens* plant named 'KLENI05081' as illustrated and described.

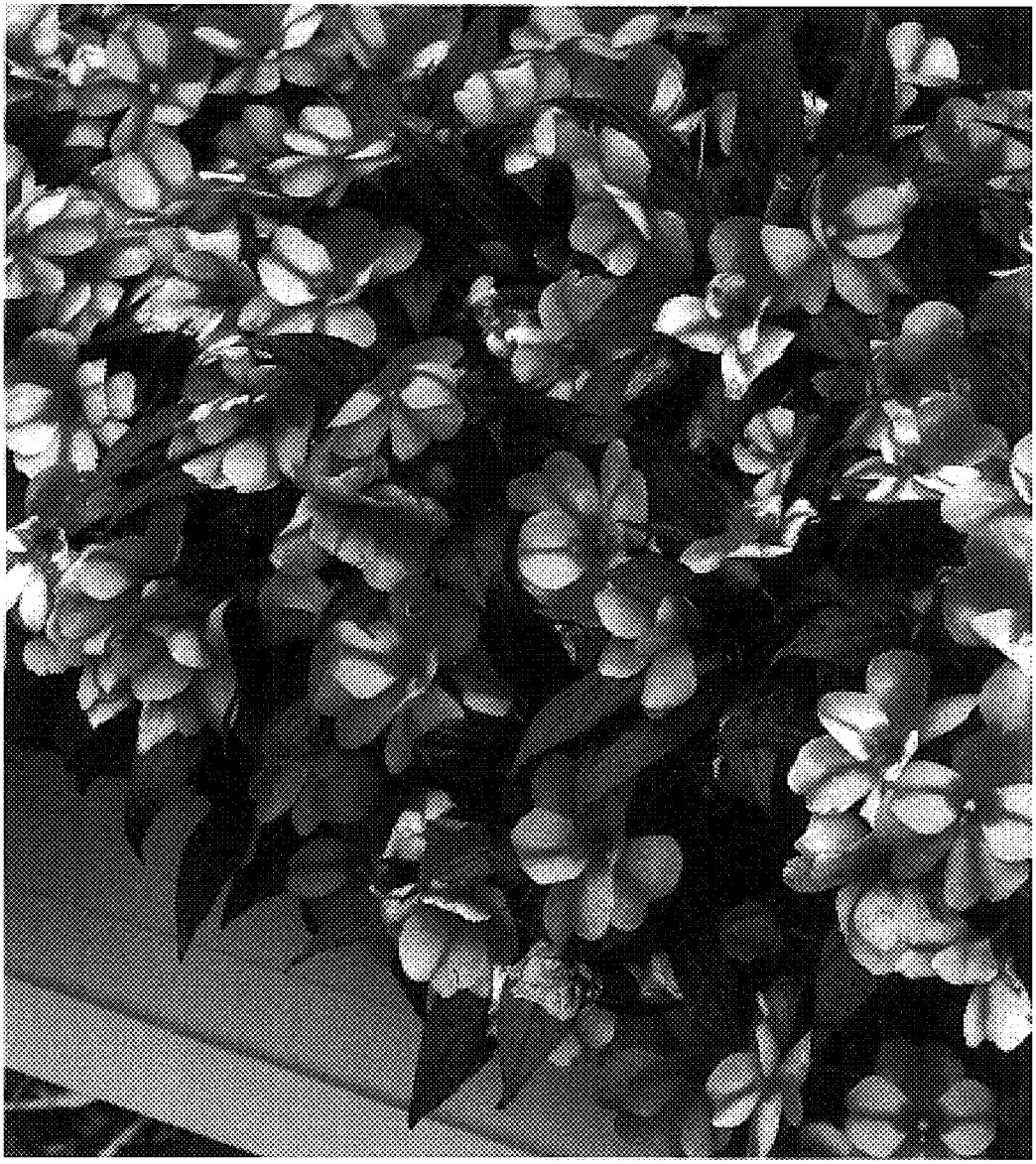

* * * * *